United States Patent [19]

Barker

[11] Patent Number: 4,663,287

[45] Date of Patent: May 5, 1987

[54] BIOLOGICALLY ACTIVE CONJUGATES AND THEIR PREPARATION AND USE

[75] Inventor: Sydney A. Barker, Birmingham, United Kingdom

[73] Assignee: Gist-Brocades N.V., Delft, Netherlands

[21] Appl. No.: 620,456

[22] Filed: Jun. 14, 1984

[30] Foreign Application Priority Data

Jun. 15, 1983 [EP] European Pat. Off. ........ 83200886.6

[51] Int. Cl.$^4$ .......................... C12N 9/96; C12Q 1/40; C12Q 1/38; C11D 17/00
[52] U.S. Cl. ...................................... 435/188; 435/22; 435/23; 252/174.12; 252/174.23; 252/DIG. 12; 530/300; 530/350; 530/354
[58] Field of Search ........................... 435/22, 23, 188; 260/112 R; 252/174.12, 174.23, DIG. 12; 530/300, 350, 354

[56] References Cited

FOREIGN PATENT DOCUMENTS 1174854 12/1969 United Kingdom .
527203 1/1980 U.S.S.R. .

OTHER PUBLICATIONS

A. B. Salleh et al., Biotechnology Letters, vol. 4(6), pp. 387–392 (1982).
J. J. Marshall et al., Biotechnology and Bioengineering, vol. XIX, pp. 1739–1760 (1977).
J. J. Marshall et al., Biotechnology and Bioengineering, vol. XVIII, pp. 1325–1329 (1976).
R. McDowell, J. Soc. Cosmet. Chem., vol. 21, pp. 441–457 (1970).

Primary Examiner—Sidney Marantz
Assistant Examiner—Patricia L. DeSantis
Attorney, Agent, or Firm—Bierman & Muserlian

[57] ABSTRACT

Water-soluble, biologically active conjugates comprising residues of (1) a biologically active protein or glycoprotein having primary amino groups, (2) a heteropolymer of D-mannuronic acid and L-guluronic acid and (3) an alkyleneglycol of 2 to 6 carbon atoms, the said residue (2) being linked to (1) by an amide linkage and to (3) by an ester linkage, which conjugates have increased activity at higher pH values and higher temperatures and a process for their preparations.

18 Claims, No Drawings

BIOLOGICALLY ACTIVE CONJUGATES AND THEIR PREPARATION AND USE

The invention relates to water-soluble biologically active conjugates of biologically active proteins and glycoproteins, especially enzymes, and to their preparation and use.

In British Patent Specification No. 1,174,854 conjugates are disclosed of certain polysacchardes, such as pectin, pectic acid, alginic acid, celluronic acid, carrageenan and lichenin uronic acid, and biologically active substances containing basic amino or phenolic hydroxyl groups. These conjugates may be used in reagent systems employing a water-soluble form of a biologically active substance which can be insolubilized or is insolubilized, in situ, the conjugate retaining its activity throughout. An example of such a system is the use of a soluble conjugated enzyme in a reaction system and then the removal of the conjugate by the addition of calcium ions. Such conjugates have been prepared by known methods for the linking of complex organic compounds containing basic amino or phenolic hydroxyl groups to the said acids, using a coupling reagent, such as a water-soluble diimide, ethyl chloroformate in the presence of a water-soluble diimide, hydrazine hydrate followed by nitrous acid, or sulphur trioxide-N,N-dimethyl formamide complex.

USSR Patent No. 707924 discloses water-soluble proteolytic enzymes modified with polysaccharides, for use in medicinal enzymology and biochemical research. Such enzymes have been prepared by reacting equimolar amounts of a proteolytic enzyme and alginic acid at pH 7.5 and isolating the product after acidification to pH 1.0–1.5. The alginic acid is prepared by lyophilizing acid precipitated alginate.

Biotechnology Letters 4 (1982), 387–392, discloses that propylene glycol alginate forms strong, covalently bonded gels when mixed with gelatin under alkaline conditions. Certain enzymes, beta-glucosidase, glucose oxidase and uricase were immobilized on the alginate ester prior to the introduction of the gelatin.

In Biotech. Bioeng. 18 (1976) 1325 and 19 (1977), 1739 conjugates of enzymes and dextran or carboxymethyl dextran are described, which are prepared by using toxic coupling agents, for example cyanogen bromide.

In J. Soc. Cosmet. Chem. 21 (1970), 441–457, the reaction of propylene glycol alginate and gelatin is described, leading to insolubilization of the gelatin. Gelatin films thus modified may be subjected to subsequent photographic processing at higher temperatures than is possible with unmodified gelatin. According to the authors a possible use of this gelatin modifying process is in the manufacture of hard gelatin capsules.

The present invention provides biologically active conjugates of biologically active proteins or glycoproteins and polysaccharide derivatives, which may be prepared by an economical simple procedure in which the by-products of the reaction are neither deleterious to the conjugate nor toxic. The conjugates have valuably modified biological properties, as compared with the parent proteins per se.

The novel water-soluble biologically active conjugates of the present invention comprise residues of (1) a biologically active protein or glycoprotein having primary amino groups, (2) a heteropolymer of D-mannuronic acid and L-guluronic acid, preferably alginic acid and (3) an alkylene glycol of 2 to 6 carbon atoms, preferably 1,2-propylene glycol, the said residue (2) being linked to (1) via amide and optionally also, ester linkages and to (3) via ester linkages, the said conjugate showing the biological activity of the said protein or glycoprotein.

According to a feature of the invention, the aforesaid new conjugates are made by mixing a biologically active protein or glycoprotein having primary amino groups, with a water-soluble alkylene glycol ester of a heteropolymer of D-mannuronic acid and L-guluronic acid in aqueous medium, the said ester preferably being sufficiently highly esterified not to form a water-insoluble calcium salt, raising the pH of the said medium sufficiently to cause partial (but not complete) reaction of the ester groups of the said ester with the amino groups of the said protein, and then lowering the pH of the said medium to terminate the reaction.

The new conjugates can be derived entirely from ingredients normally permitted in foods such as propylene glycol alginate and food grade enzymes. The synthesis only involves the use of alkaline conditions for short periods of time at ambient temperatures so that the risk of denaturing the protein is much reduced. No toxic coupling reagent is required. Only commercially available starting material are required, and complicated and costly steps, such as lyophilization, are avoided.

The conjugates of the invention possess important technical advantages as compared with the parent proteins, e.g. enzymes. In particular, a conjugated enzyme retains its activity at higher pH, and higher temperatures than the parent enzyme. The possibility of extending the pH-range of enzyme activity to a higher pH permits the simple combination of enzyme processes where previously, because of the difference in pH optima, two or more consecutive enzyme steps have been performed. By converting the enzyme with the lower pH optimum to a conjugate having a higher pH-optimum, both steps can be combined, which is advantageous economically. The thermal stability of enzymes is also enhanced by conjugation.

The new conjugates are normally made in aqueous solution. The coupling reaction of the alginate ester and the protein is catalysed by a reagent which raises the pH such as an alkali metal hydroxide, carbonate or bicarbonate or a mixture thereof. The reaction may be carried out in the presence of a polyhydric alcohol such as glycerol or sorbitol, and calcium ions.

The type of heteropolymer ester useful in the invention is a highly esterified alkylene glycol ester, preferably the 1,2-propylene glycol ester of a polyuronic acid containing D-mannuronic and L-guluronic acid residues in M/G ratios within the range 0.1 to 10, preferably 0.3 to 1.5, and most advantageously about 1. Such esters, which are alginic acid esters, are commercially available, e.g. as Manucol Ester E/RE. The aqueous concentration of the heteropolymer ester in the reaction mixture should be about 1%–5% w/v, preferably about 3%, in admixture with the biologically active protein, immediately prior to the adjustment to an alkaline pH.

Alkali metal hydroxides, carbonates or bicarbonates or mixtures thereof are advantageously used to provide the source of the alkalinity. Preferably the pH of the reaction medium is adjusted to between 9.5–10.5, preferably 10.0. The reaction is best effected in aqueous media at below 50° C. and advantageously at ambient temperature. The reaction has normally progressed sufficiently within 1–60 minutes, and usually about 10 minutes, and the reaction is then stopped by adjustment of the medium to a neutral pH. With alkali labile proteins, the time at an alkaline pH may be shortened still further. Although it is usual to terminate the reaction by adjustment of the pH to neutrality, there is no objection to any pH in the range of 3–9 since the reaction does not proceed and the conjugates are stable within this range.

Examples of biologically active proteins which may be converted into conjugates are industrial enzymes such as proteases, and preferably alkaline proteases, polysaccharide hydrolases, lipases, glucose isomerase, lactase, glucoamylase, alpha-amylase, including thermostable amylase, glucose oxidase, catalase, and invertase. Experiments with amino group blocking reagents have shown that the link between the alginate ester and the protein is mainly amide. For example, when the enzyme is first reacted with fluorescein isothio-cyanate, blocking its available amino groups, a conjugate is only obtained in small yield on subsequent reaction with propylene glycol alginate. Any biologically active protein or glycoprotein having free amino groups may therefore be used for preparing the conjugate.

The invention is further illustrated by the following Examples. In the Examples the general methods of analysis were conducted as follows.

Determination of hexuronic acid by the Method of Dische (Carbazole assay)

Carbazole (recrystallized from ethanol, 100 mg) was dissolved in ethanol (spectroscopic grade, 100 ml). An aliquot (1.0 ml) of sample (containing between 0 and 100 µg of hexuronic acid) was mixed, with cooling, with 6 ml of sulphuric acid (M.A.R., 98% v/v) contained in a borosilicate glass test tube (12 ×1.5 cm). This was placed in a boiling water bath and heated for 20 minutes. The solution was cooled to room temperature and 0.2 ml of carbazole reagent added with shaking. After standing at room temperature for 45 minutes, the optical density was determined at 530 nm. A standard plot was prepared.

Glucose Determination by Glucose Oxidase Assay

This calibration makes it possible to obtain directly the glucose concentration from the knowledge of an absorbance reading.

Glucose oxidase (Sigma Chemical Co., E.C.1.1.3.4; ex. *Aspergillus niger*, 19.500 Units/g) 50 mg, peroxidase (Sigma Chemical Co., E.C.1.11.1.7; ex. horseradish, 90 purpurogallin Units/mg, 10 mg) and 2,2'-azino-di-(3-ethyl) thiazoline sulphonic acid)-diammonium salt (ABTS, Sigma Chemical Co., 50 mg) diluted to 400 ml with TMS-hydroxymethyl-methylamine (TRIS) buffer (0.125M, pH 7.0). The solution was stored at 0° C.

Concentrations of D-glucose were made up in the range 10–80 µg/ml in TRIS buffer. Samples of each of these concentrations (0.01 ml) were added to reagent (1.0 ml). The reaction mixtures were incubated at 37° C., the optimum temperature for glucose oxidase, in a water bath for 15 minutes. The absorbance was then measured at 420 nm for each glucose concentration.

Determination of 1,2-dihydroxypropane (propylene glycol, P.G.).

Acetaldehyde has been reported to interfere in the resorcinol assay for fructose by shifting the wavelength of maximum absorption of the chromophore from 480 to 555 nm. This interference makes possible the quantitative determination of acetaldehyde in the presence of fixed quantities of fructose. 1,2-Dihydroxypropane is oxidised by periodic acid to acetaldehyde. The assay method for propylene glycol (P.G.) is based on this system.

Sample solutions (0.1 ml) containing propylene glycol 5–50 µg/ml were pipetted into stoppered test-tubes and a solution of periodic acid (25 mM) in sulphuric acid (62.5 mM, 0.1 ml) were added. The solutions were maintained for 30 minutes at room temperature. Then sodium metabisulphite (1M; 0.05 ml) were added. After 5 min. D-fructose (0.4 mM, 0.25 ml) were added, followed by a resorcinol reagent (3.0 ml) prepared immediately before use by addition of A.R.-grade hydrochloric acid (10 vol) to a stock aqueous solution of resorcinol (12 mM, 1 vol). Solutions were heated at 80° C. for 5 min. and then cooled to room temperature, and the absorbance of the characteristic red chromophore was measured at 555 nm.

Using this method the following standard curve was made:

| P.G. µg/ml | O.D. 555 nm |
|---|---|
| 5 | 0.2 |
| 10 | 0.27 |
| 16.5 | 0.365 |
| 20 | 0.385 |
| 33 | 0.45 |
| 50 | 0.47 |

The results were plotted and an essentially straight line was obtained which became asymptotic at concentrations higher than 30 µg/ml.

Amylochrome Assay for Alpha-Amylase Activity

Alpha-amylase hydrolyses water-insoluble amylose covalently bound to a blue dye into soluble saccharides without attacking the bond to the dye. The colour intensity of the blue solution obtained is directly proportional to the amylase activity of the sample.

Reagents

| 1. Substrate: | Amylose-Cibacron ® Blue F3GA Phosphate buffer pH 7.0, 50 µmole/tablet |
|---|---|
| 2. Diluent: | NaH$_2$PO$_4$ 50 mM/bottle (pH 4.3) The diluent is dissolved before use in 500 ml of distilled water ("diluent solution") |
| 3. Standard: | Cibacron Blue F3GA corresponding to 460 U/l alpha-amylase |

Procedure

A standard solution (S) was prepared by dissolving 1 tablet of the Substrate in 1 ml of distilled water and the solution was heated for 5 min. at 37° C. Then 0.05 ml of the Standard was added, well mixed by vortexing and the mixture was incubated for exactly 15 min. at 37° C. The reaction was stopped by addition of 4 ml of the diluent solution. The mixture was centrifuged for 10 min. at approx. 3000 r.p.m.

In the same way a test solution (T) was prepared, but now 0.05 ml of a test sample was added instead of the Standard. Finally a blank solution (TB) was prepared by using the same procedure as for the preparation of the (S) and (T) solutions, but without 0.05 ml of the Standard and the test sample, respectively.

The absorbance of (T) was measured at 620 nm against the absorbance of the (TB) in the supernatant, giving a value A(T). The absorbance of (S) was measured at 620 nm against distilled water, giving a value A(S).

The activity of the alpha-amylase solution was calculated using the formula:

$$c\ (U/I) = \frac{A(T)}{A(S)} \times 460$$

where 1 U/I (international unit) corresponds to the formation of 1 µ-equivalent of reducing groups per litre per minute.

DNS - assay

An aliquot (0.1 ml) of the diluted enzyme solution is mixed with soluble starch (2.0 ml, 1% w/v in acetate, pH 6.5, 50 mM, 5 mMCa$^{2+}$) and samples (0.1 ml) removed at 0.5, 5, 10 and 15 minute intervals. These are pipetted into D.N.S. reagent (1.0 ml)*, heated for 8 minutes at 99° C., cooled and the absorbance read at 520 nm against a reagent blank. A maltose (1 mg/ml) standard is included at each assay.

* DNS reagent: 3,5-Dinitrosalicylic acid (1 mg/cm$^3$), potassium sodium tartrate.4H$_2$O (300 mg/cm$^3$) in aqueous sodium hydroxide (0.4 M). DNS reagent stored in the absence of light until used.

EXAMPLE 1

Preparation of Alpha-Amylase-Alginate Ester Conjugate

1% (w/v) solution of purified alpha-amylase (derived from B. subtilis) in distilled water (2 ml) was mixed with 5% (w/v) solution of Manucol ester E/RE in distilled water (4 ml). A sample was taken (=sample 1, unreacted mixture).

Next the pH of the mixture was raised to 10 by addition of a 10% (w/v) solution of sodium carbonate. After 20 minutes the pH was lowered to 6.5 by addition of acetic acid (1.0 M). Again a sample was taken (=sample 2, reacted mixture).

Samples 1 and 2 were each loaded on a Sephadex G-200 column and eluted with acetate buffer pH 6.5 (50 mM) Eluted fractions were assayed for amylase activity (Amylochrome assay).

The shape of the elution curves shows that part of the amylase activity in sample 2 (reacted mixture) eluted at lower elution volumes compared to the unreacted mixture, indicating an increase in molecular weight caused by conjugate formation.

EXAMPLE 2

Determination of the Relative Activity of Enzyme Conjugate and Free Enzyme on Soluble and Insoluble Substrate An alpha-amylase-conjugate was prepared as in Example 1, and fractionated on Sephadex G-200. The fractions containing the conjugate (18-46 ml) were pooled, and so were the fractions containing the free enzyme (46-66 ml). Both pools and also the alpha-amylase used to prepare the conjugate were subjected to the DNS-assay (soluble substrate) and the amylochrome assay (insoluble substrate), and the ratio DNS-activity/amylochrome-activity calculated for each sample.

The ratio for the alpha-amylase starting material is represented by R.

Results:

| Enzyme preparation | DNS/amylochrome ratio |
|---|---|
| alpha-amylase, starting material | R |
| alpha-amylase, free enzyme from Sephadex separation | R |
| alpha-amylase conjugate from Sephadex separation | 2.7 R |

The results indicate that, per unit of DNS, activity the conjugate fraction shows a 2.7 times lower activity towards insoluble substrate compared to the free enzyme fraction and the alpha-amylase starting material. A ratio exceeding R is indicative of conjugate formation.

EXAMPLE 3

Preparation of Thermostable Alpha-Amylase Conjugate

To a solution of Manucol ester E/RE in distilled water (3%, 15 ml) adjusted to pH 7 was added 5 ml of a crude, liquid preparation of thermostable alpha-amylase derived from B. licheniformis, containing 4 mg of enzyme/ml. The pH was raised to 10 by dropwise addition of sodium hydroxide (1.0 N) During the course of the reaction the pH dropped and was readjusted three times to pH 10. After 15 minutes, the pH was lowered to 6.5 by addition of HCl (1.0 N). Final volume was 25 ml.

A sample of this preparation (5 ml) was applied to a Sephadex G-200 bolumn and eluted with acetate buffer (pH 6.5) containing calcium chloride (0.05 M). 2.0 ml fractions were collected which were assayed for alpha-amylase activity.

The conjugate containing fractions were pooled and freed from salts by dialysis overnight against distilled water. The solution was then freeze dried. 12 mg of the freeze dried material was dissolved in 4 ml of distilled water. 2 ml of 0.5 M sodium hydroxide were added to raise the pH to 12, and the solution was then allowed to stand overnight. The propylene glycol released was determined. The results show that the conjugate still contained 10% of the propylene glycol originally present in the Manucol ester E/RE.

Example 4

Variation of Enzyme: Alginate Ester Ratio During Conjugation

Manucol Ester E/RE (0, 40, 80 or 120 mg) was added to 4 ml of Maxamyl LX 6000 (a commercially available liquid preparation of Gist-Brocades N.V., containing 60% w/v glycerol, and 75 mg/ml of alpha-amylase derived from B. subtilis), and solution effected. The conjugation reaction was effected as in Example 1 using a reaction time of 15 minutes.

The reaction products were assessed for conjugation by comparison of the DNS/Amylochrome ratio as described in Example 1.

| Sample | LX 6000 containing glycerol | Conjugated reaction product | | |
|---|---|---|---|---|
| | | 1% | 2% | 3% alginate ester reacted |
| DNS/Amylochrome ratio | R | 1.45 R | 1.87 R | 2.29 R |

As a high ratio is indicative of conjugation, the results show that a high ratio of alginate ester to enzyme is beneficial in achieving conjugation. It should be noted that in this case the complete reaction mixture was assayed, without prior Sephadex fractionation.

EXAMPLE 5

Large Scale Preparation of Maxamyl LX-6000 Manucol Esters E/RE Conjugate

A solution of Manucol ester E/RE in distilled water (5% w/v, 250 ml) was added gradually with stirring to 250 ml of Maxamyl LX-6000 (see Example 4) and the pH of the solution was raised to pH 10 by addition of sodium hydroxide (1.0 M). During the course of the reaction the pH dropped to 9.5 and was readjusted twice to pH 10. After 45 minutes the pH was adjusted to 6.5 by addition of hydrochloric acid (1.0 M). The final volume was 600 ml.

A sample of this preparation (1.9 ml) was applied to a Sephadex G-200 column and eluted with acetate buffer (pH 6.5) containing calcium chloride (0.05 M). The conjugate containing fractions were pooled and used for thermal stability studies (see Example 6).

EXAMPLE 6

Determination of Thermal Stability of Alpha-Amylase Conjugate

In order to test the relative thermal stabilities of Maxamyl LX 6000 and its conjugate with Manucol ester E/RE, the enzymes were mixed with a large excess of a 3% (w/v) suspension of corn starch in distilled water containing 0.05 M of calcium chloride, and adjusted to pH 6.5 with sodium carbonate.

The mixtures were incubated for 40 minutes at 70° C., 80° C. and 90° C. A sample was then removed and assayed for glucose content by the glucose oxidase method. The amount of glucose liberated is a measure for the activity of the enzyme preparations.

| Results: (expressed as % of the activity at 70° C.) | | | |
|---|---|---|---|
| | 70° C. | 80° C. | 90° C. |
| Maxamyl LX 6000 conjugate | 100% | 76% | 46% |
| Maxamyl LX 6000 | 100% | 55% | 18% |

The conjugate shows improved activity retention at higher temperatures compared to Maxamyl LX 6000.

EXAMPLE 7 pH-Activity Profile of Amylase Conjugate

An amylase-alginate ester conjugate was prepared and purified on Sephadex as described in Example 1.

The starting material (purified alpha-amylase) and its conjugate were incubated at 80° C. with a 3% (w/v) solution of soluble starch (containing 5 mM of $CaCl_2$) for 40 minutes, at various pH-values. Samples were then assayed for glucose by the glucose oxidase method.

| Results: | | |
|---|---|---|
| | Activity expressed as % of maximum value | |
| pH | alpha-amylase | alpha-amylase conjugate |
| 4 | 0% | 0% |
| 5 | 8% | 9% |
| 6 | 87% | 93% |
| 6.5 | 100% | 98% |
| 7 | 91% | 100% |
| 8 | 73% | 96% |

Compared to the normal alpha-amylase, the pH-activity curve for the alpha-amylase conjugate is shifted to higher pH-values.

EXAMPLE 8

Conjugation of Lactase

To 5 ml of Maxilact ®LX 5000 (a commercially available liquid of Gist-Brocades N.V., glycerol-containing, preparation of lactase derived from the yeast *Kluyveromyces lactis*) 5 ml of a 6% (w/v) solution of Manucol ester E/RE in distilled water was added.

The mixture was cooled to 10° C., and the pH was raised to 10.2 by addition of 1.0 M sodium hydroxide. The mixture was stirred for 12 minutes. Then the pH was lowered to 5.2 by addition of 1.0 M hydrochloric acid, and finally adjusted to 6.95 using 0.2 M $Na_2HPO_4$ solution.

A sample of the final mixture was diluted with distilled water (5×) and loaded on a Sepharose B column (bed volume 36.4 ml). The column was eluted at 4° C. with phosphate buffer pH 7 (0.1 M). Fractions were collected and tested for lactase activity and alginate content (carbazole assay).

Sepharose B fractionation (the alginate assay excepted) was also performed on a mixture of Maxilact LX 5000 with sodium alginate. The results show that: the lactase activity is eluted as a single peak; presence of sodium alginate (which is formed from alginate ester under alkaline conditions) does not change this elution pattern; after conjugation the enzyme activity is eluted in two separate peaks, and so is the alginate; the first activity peak coincides with the first alginate peak, indicating that a conjugate is formed; this conclusion is strengthened by the fact that the second activity peak (unconjugated enzyme) and the second alginate peak (unconjugated alginate) do not coincide.

EXAMPLE 9

Determination of the pH-Activity Profile of Conjugated Lactase

The relative activity at various pH-values was determined for:
the reacted mixture from Example 8;
an unreacted mixture of Maxilact LX 5000 and Manucol ester E/RE.

Results are expressed as percentage of the activities at pH 6:

| pH | Reacted mixture | Unreacted mixture |
|---|---|---|
| 6 | 100% | 100% |
| 7 | 113% | 88% |
| 8 | 96% | 54% |
| 9 | 47% | 29% |

Results show a shift towards higher pH values for the conjugated product.

EXAMPLE 10

Heat Stability of Conjugated Maxilact LX 5000

Manucol ester E/RE (500 mg) was dissolved in 15 ml Maxilact LX 5000. Part of this mixture was set aside for later testing. The remainder was cooled to 10° C., and 0.4 ml of 1M NaOH was added to raise the pH to 10.35. After stirring for 10 minutes the pH was lowered to 6.75 by addition of 0.4 ml of 1M HCl, and adjusted to 7.0 with 0.2M Na$_2$HPO$_4$.

Both the reacted (unpurified) and the unreacted mixture were diluted with distilled water, and incubated at 44° C. Samples were withdrawn after 0, 5, 10, 15, 20 and 30 minutes, and the residual lactase activity was determined.

The results, expressed as percentage of the residual activity after 0 minutes incubation, are shown in the following table.

| Incubation time at 44° C. (minutes) | Unreacted mixture | Reacted mixture |
|---|---|---|
| 0 | 100% | 100% |
| 5 | 60% | 99% |
| 10 | 51% | 98% |
| 15 | 46% | 96% |
| 20 | 43% | 96% |
| 30 | 34% | 98% |

What I claim is:

1. A water-soluble, biologically active conjugate comprising residues of (1) a biologically active enzyme having primary amino groups, (2) a heteropolymer of D-mannuronic acid and L-guluronic acid and (3) an alkyleneglycol of 2 to 6 carbon atoms, said residue (2) being linked to (1) by an amide group and to (3) by an ester group and wherein said conjugate excludes propylene glycol alginate with beta-glucosidase, glucose oxidase or uricase.

2. A conjugate of claim 1 wherein the alkylene glycol is 1,2-propyleneglycol.

3. The conjugate of claim 1 wherein the heteropolymer is alginic acid.

4. The conjugate of claim 1 or 2 or 3 wherein the protein is an enzyme selected from the group consisting of alpha-amylase, lactase, high-alkaline protease and glucoamylase.

5. A method of effecting an enzyme-substrate reaction comprising contacting a conjugate of claim 4 with a substrate for the enzyme of the conjugate.

6. The method of claim 5 wherein the protein is thermally stable alpha-amlase.

7. The conjugate of claim 1 or 2 or 3 wherein the enzyme is thermally stable alpha-amylase.

8. A process for the preparation of a water-soluble, biologically active conjugate of claim 1 comprising (1) mixing in an aqueous medium a biologically active enzyme having primary amino groups with a water-soluble. alkylene glycol ester of a heteropolymer of D-mannuronic acid and L-guluronic acid, (2) raising the pH to about 10 to effect partial reaction of the ester group with the amino groups of the protein and (3) lowering the pH to about 5 to terminate the reaction.

9. The process of claim 8 wherein the concentration of the alkylene glycol ester is about 3% w/v.

10. The process of claim 8 wherein the pH is raised to 9.5 to 10.5.

11. The process of claim 8 or 10 wherein the pH is lowered to 3 to 9.

12. The process of claim 8 or 10 wherein the alkylene glycol is 1,2-propyleneglycol.

13. The process of claim 8 or 10 wherein the heteropolymer is alginic acid.

14. The process of claim 8 or 10 the protein is an enzyme selected from the group consisting of alpha-amylase, lactase, high-alkaline protease and glucoamylase.

15. The process of claim 8 or 10 wherein the enzyme is thermally stable alpha-amylase.

16. The process of claim 8 or 10 wherein the initial concentration of the alkylene glycol ester in the aqueous medium is 1 to 5% W/V.

17. A process for effecting an enzyme substrate reaction of a water-soluble, biologically active conjugate comprising mixing residues of (1) a biologically active enzyme having primary amino groups, (2) a heteropolymer of D-mannuronic acid and L-guluronic acid and (3) an alkyleneglycol of 2 to 6 carbon atoms, linking said residue (2) to (1) by an amide group and to (3) by an ester group.

18. A method of preparing gelatin capsules comprising mixing residues of (1) a biologically active enzyme having primary amino groups, (2) a heteropolymer of D-mannuronic acid and L-guluronic acid and (3) an alkyleneglycol of 2 to 6 carbon atoms, linking said residue (2) to (1) by an amide group and to (3) by an ester group.

* * * * *